(12) United States Patent
Wulfman et al.

(10) Patent No.: US 8,929,997 B2
(45) Date of Patent: Jan. 6, 2015

(54) ACTIVE FIXATION LEADS AND METHOD OF ASSEMBLY

(71) Applicant: Cardiac Pacemakers, Inc., St. Paul, MN (US)

(72) Inventors: David R. Wulfman, Minneapolis, MN (US); Douglas D. Pagoria, Forest Lake, MN (US); Joseph C. Walker, Shoreview, MN (US)

(73) Assignee: Cardiac Pacemakers Inc., St. Paul, MN (US)

( * ) Notice: Subject to any disclaimer, the term of this patent is extended or adjusted under 35 U.S.C. 154(b) by 0 days.

(21) Appl. No.: 14/107,361

(22) Filed: Dec. 16, 2013

(65) Prior Publication Data

US 2014/0107753 A1  Apr. 17, 2014

Related U.S. Application Data

(62) Division of application No. 13/088,017, filed on Apr. 15, 2011, now Pat. No. 8,634,933.

(60) Provisional application No. 61/345,411, filed on May 17, 2010.

(51) Int. Cl.
*A61N 1/00* (2006.01)
*A61N 1/05* (2006.01)
*A61N 1/375* (2006.01)

(52) U.S. Cl.
CPC .............. *A61N 1/0587* (2013.01); *A61N 1/056* (2013.01); *A61N 1/057* (2013.01); *A61N 1/0575* (2013.01); *A61N 1/375* (2013.01)

USPC ......................................................... 607/116

(58) Field of Classification Search
CPC ...... A61N 1/057; A61N 1/0587; A61N 1/375; A61N 1/0575; A61N 1/056
USPC ........... 607/116–117, 127, 131; 600/375, 377
See application file for complete search history.

(56) References Cited

U.S. PATENT DOCUMENTS

| 4,402,329 | A | * | 9/1983 | Williams ...................... 607/123 |
| 5,303,704 | A | * | 4/1994 | Molacek et al. .............. 600/377 |
| 5,324,321 | A | * | 6/1994 | Pohndorf et al. ............. 607/116 |
| 5,476,497 | A | * | 12/1995 | Mower et al. ................. 607/122 |
| 5,584,873 | A | * | 12/1996 | Shoberg et al. ............... 607/122 |
| 5,957,970 | A | * | 9/1999 | Shoberg et al. ............... 607/122 |

(Continued)

FOREIGN PATENT DOCUMENTS

| JP | 2002512096 A | 4/2002 |
| WO | WO2010019654 A1 | 2/2010 |
| WO | WO2010019654 | * 2/2010 |

OTHER PUBLICATIONS

International Serach Report and Written Opinion issued in PCT/US2011/032851, mailed Jun. 27, 2011, 12 pages.

*Primary Examiner* — Mark W Bockelman
(74) *Attorney, Agent, or Firm* — Faegre Baker Daniels LLP

(57) ABSTRACT

An active fixation lead may have a lead body formed at least in part from an inner member and an outer sheath. The inner member may include a pace/sense lumen and one or more cable lumens. The inner member may include one or more longitudinally extending crumple zones that are configured to reduce stress within the pace/sense lumen that could otherwise be caused by compressive forces applied to the lead.

11 Claims, 8 Drawing Sheets

(56) References Cited

U.S. PATENT DOCUMENTS

| | | |
|---|---|---|
| 6,263,224 B1 | 7/2001 | West |
| 6,741,893 B2 * | 5/2004 | Smits .......................... 607/122 |
| 6,983,185 B2 | 1/2006 | Ley et al. |
| 7,027,851 B2 | 4/2006 | Mejia |
| 7,245,973 B2 | 7/2007 | Liu et al. |
| 7,289,846 B2 * | 10/2007 | Shoberg et al. .................. 607/2 |
| 7,630,749 B2 | 12/2009 | Squeri |
| 7,657,326 B2 | 2/2010 | Bodner et al. |
| 7,774,934 B2 | 8/2010 | Sundberg et al. |
| 8,406,898 B2 | 3/2013 | Wulfman |
| 2003/0069625 A1 | 4/2003 | Ley et al. |
| 2003/0163184 A1 | 8/2003 | Scheiner et al. |
| 2005/0137671 A1 | 6/2005 | Liu et al. |
| 2006/0089698 A1 | 4/2006 | Sundberg et al. |
| 2008/0109042 A1 | 5/2008 | Bodner et al. |
| 2009/0088811 A1 | 4/2009 | Wulfman |
| 2009/0259272 A1 | 10/2009 | Reddy et al. |

* cited by examiner

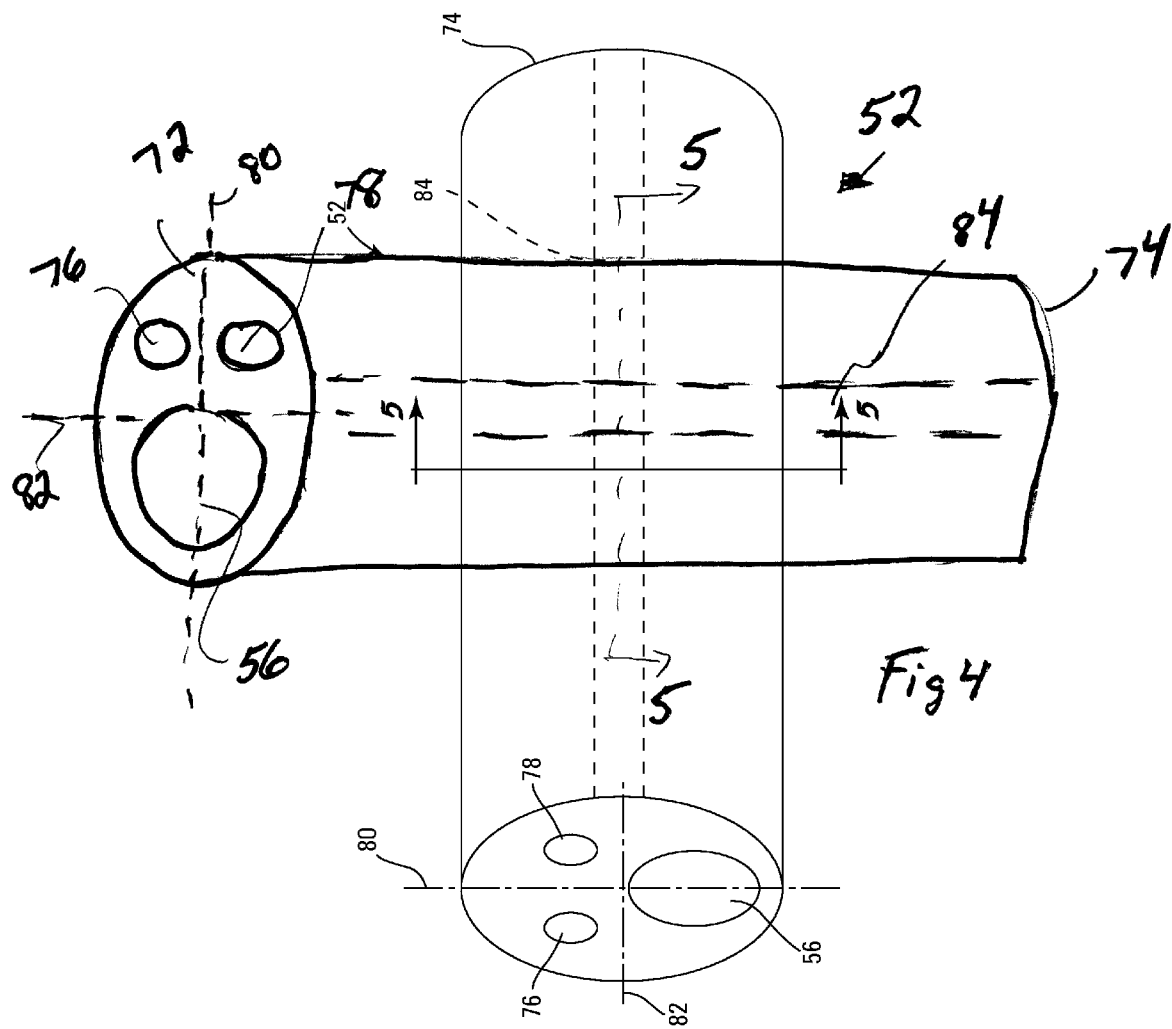

ACTIVE FIXATION LEADS AND METHOD OF ASSEMBLY

CROSS-REFERENCE TO RELATED APPLICATION

This application is a division of U.S. patent application Ser. No. 13/088,017, filed Apr. 15, 2011, and entitled "ACTIVE FIXATION LEADS AND METHOD OF ASSEMBLY," which claims the benefit under 35 U.S.C. §119(e) to U.S. Provisional Patent Application 61/345,411, filed on May 17, 2010, the entire contents of which are incorporated herein by reference in their entirety.

TECHNICAL FIELD

The present invention relates to implantable medical devices and relates more particularly to leads for cardiac rhythm management (CRM) systems.

BACKGROUND

Various types of medical electrical leads for use in cardiac rhythm management (CRM) and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

Various implantable leads are disclosed herein. Example 1 is an implantable lead having an elongate body extending between a proximal region and a distal region. The elongate body includes an outer sheath and an inner member that is disposed within the outer sheath. The inner member includes a coil lumen, a conductor lumen and one or more longitudinally extending crumple zones that are arranged in an outer surface of the inner member. The lead includes a connector assembly that is secured to the proximal region for coupling the lead to an implantable medical device. The connector assembly includes a terminal pin that is rotatable relative to the body. A conductor coil is disposed longitudinally within the coil lumen, is coupled to the terminal pin and is rotatable relative to the body. A conductor cable is disposed longitudinally within the cable lumen. A coupler is rotatably disposed within the distal region of the elongate body and is connected to the conductor coil. A fixation helix is secured to the coupler. An electrode is disposed about the distal region of the elongate body and is electrically connected to the conductor cable. The terminal pin is rotatably engaged with the couple via the conductor coil such that rotation of the terminal pin causes the coupler and the fixation helix to rotate and therefore translate relative to the elongate body.

In Example 2, the implantable lead of Example 1 in which the one or more longitudinally extending crumple zones define void spaces between the outer sheath and the inner member.

In Example 3, the implantable lead of Example 1 or Example 2 in which the outer surface of the inner member has an at least substantially circular cross-sectional profile outside of the one or more crumple zones.

In Example 4, the implantable lead of any of Examples 1-3 in which the one or more crumple zones include a pair of crumple zones, each of the pair of crumple zones being arranged on an opposing side of the inner member.

In Example 5, the implantable lead of Example 4 in which each of the pair of crumple zones include an elongate groove having an apex thereof.

In Example 6, the implantable lead of Example 5 in which each of the elongate grooves has a width, measured at the outer surface of the inner member, of about 0.008 inches to about 0.0105 inches, and a depth measured perpendicular to the width, of about 0.010 inches to about 0.015 inches.

In Example 7, the implantable lead of any of Examples 5-6 in which the apex of each of the elongate grooves defines a hinge point.

In Example 8, the implantable lead of Example 4 in which each of the pair of crumple zones include a flattened side of the inner member.

In Example 9, the implantable lead of 8 in which the inner member has a diameter measured across the flattened sides that is about 30 percent less than a diameter measured outside of the flattened sides.

Example 10 is an implantable lead body having a proximal end and a distal end. The implantable lead body includes an outer sheath extending from the proximal end to the distal end and an asymmetric multiple lumen inner member that is disposed within the outer sheath. The asymmetric multiple lumen inner member has a longitudinal axis and includes a first lumen extending through the asymmetric multiple lumen inner member, a second lumen extending through the asymmetric multiple lumen inner member and a third lumen extending through the asymmetric multiple lumen inner member. The first lumen has a first diameter, the second lumen has a second diameter and the third lumen has a third diameter. The third diameter is less than the first diameter. A pair of longitudinally extending crumple zones are arranged in an outer surface of the asymmetric multiple lumen inner member.

In Example 11, the elongate lead body of Example 10 in which the first lumen has a longitudinal axis that is offset from the longitudinal axis of the asymmetric multiple lumen inner member.

In Example 12, the elongate lead body of Example 10 or Example 11 in which the asymmetric multiple lumen inner member is symmetric about a first axis extending radially through the first lumen and between the second lumen and the third lumen, and is asymmetric about a second axis extending radially through the first lumen perpendicular to the first axis.

In Example 13, the elongate lead body of any of Examples 10-12 in which the second diameter is equal to the third diameter.

In Example 14, the elongate lead body of any of Examples 10-13 in which the pair of longitudinally extending crumple zones are configured to act as hinge points.

Example 15 is a method of manufacturing an elongate lead body that has an outer sheath and a multiple lumen internal member. The multiple lumen internal member is extruded, having a coil lumen with an extruded coil lumen cross-sectional area, a cable lumen and longitudinally extending crumple zones formed in an outer surface of the multiple lumen internal member. The extruded multiple lumen internal member is strung through the outer sheath to form the elongate lead body. The coil lumen has a strung coil lumen cross-sectional area. The strung coil lumen cross-sectional area is less than about 25 percent smaller than the extruded coil lumen cross-sectional area after the extruded multiple lumen internal member has been strung through the outer sheath.

In Example 16, the method of Example 15, further including disposing one or more electrodes about the outer sheath.

In Example 17, the method of Example 15 or Example 16, further including stringing internal components within the multiple lumen internal member.

In Example 18, the method of Example 17 in which the internal components are one or more of a coil conductor, a cable conductor or a polytetrafluoroethylene liner.

In Example 19, the method of any of Examples 15-18 in which the coil lumen has a substantially circular cross-sectional area both before and after stringing the multiple lumen internal member through the outer sheath.

In Example 20, the method of any of Examples 15-19 in which the cable lumen has a substantially circular cross-sectional area both before and after stringing the multiple lumen internal member through the outer sheath.

In Example 21, the method of any of Examples 15-20 in which the outer surface of the multiple lumen inner member has an at least substantially circular cross-sectional profile outside of the longitudinally extending crumple zones.

In Example 22, the method of any of Examples 15-21 in which each of the longitudinally extending crumple zones include an elongate groove.

In Example 23, the method of any of Examples 15-21 in which each of the longitudinally extending crumple zones include a flattened side of the multiple lumen inner member.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4 is a schematic view of a portion of the lead of FIG. 1.

Figure 1:
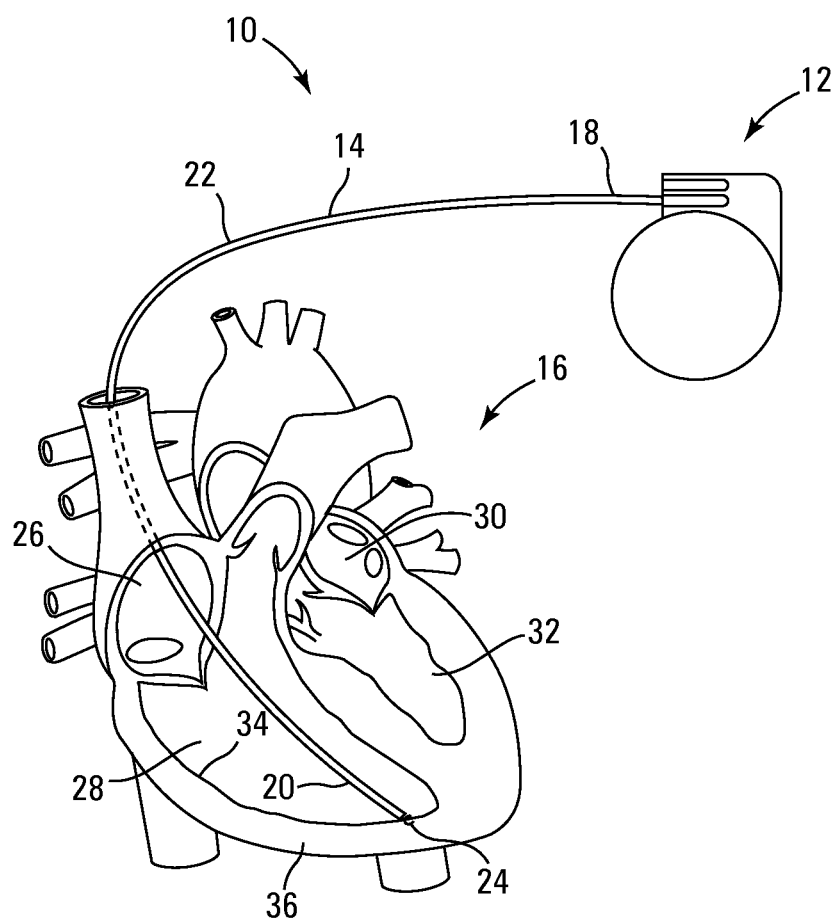
FIG. 1 is a combined cutaway and perspective view of an implantable medical device and lead in accordance with an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable cardiac rhythm management (CRM) system 10. The CRM system 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body 22 extending from the proximal region 18 to the distal region 20. The proximal region 18 is coupled to the pulse generator 12 and the distal region 20 is coupled to the heart 16. The distal region 20 includes a fixation helix 24, which, as will be discussed in greater detail below, locates and/or secures the distal region 20 within the heart 16.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for biventricular pacing, and/or includes combinations of pacing, CRT, and defibrillation capabilities, e.g., a CRT-D device.

The lead body 22 can be made from any flexible, biocompatible materials suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body characteristics to its intended clinical and operating environments. In various embodiments, the proximal and distal ends of the lead body 22 are made from different materials selected to provide desired functionalities. As will be explained with reference to subsequent figures, in some embodiments the lead body 22 may be formed from one or more separately extruded or otherwise formed tubular elements. In some embodiments, the tubular elements may be configured to provide manufacturing advantages.

As is known in the art, the heart 16 includes a right atrium 26, a right ventricle 28, a left atrium 30 and a left ventricle 32. It can be seen that the heart 16 includes an endothelial inner lining or endocardium 34 covering the myocardium 36. In some embodiments, as illustrated, the fixation helix 24, located at the distal region 20 of the lead, penetrates through the endocardium 34 and is imbedded within the myocardium 36. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26.

In the illustrated embodiment shown in FIG. 1, the fixation helix 24 penetrates the endocardium 34 of the right ventricle 28 and is embedded in the myocardium 36 of the heart 16. In some embodiments, the fixation helix 24 is electrically active and thus operates as a helical electrode for sensing the electrical activity of the heart 16 and/or applying a stimulating pulse to the right ventricle 28. In other embodiments, the fixation helix 24 is not electrically active. Rather, in some embodiments, other components of the lead 14 are electrically active.

Figure 2:
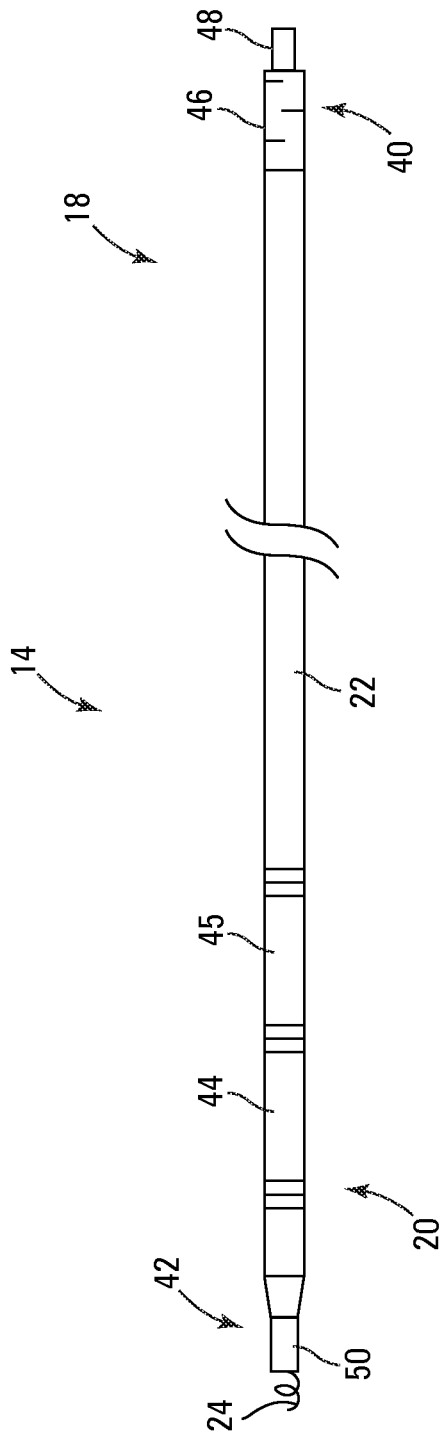
FIG. 2 is a side elevation view of the lead of FIG. 1.

FIG. 2 is an isometric illustration of the lead 14. A connector assembly 40 is disposed at or near the proximal region 18 of the lead 14 while a distal assembly 42 is disposed at or near the distal region 20 of the lead 14. Depending on the functional requirements of the CRM system 10 (see FIG. 1) and the therapeutic needs of a patient, the distal region 20 may include one or more electrodes. In the illustrated embodiment, the distal region 20 includes a pair of coil electrodes 44 and 45 that can function as shocking electrodes for providing a defibrillation shock to the heart 16. In some embodiments, one or more of the coil electrodes 44 and 45 may act as low voltage pace or sense electrodes.

In various embodiments, the lead 14 may include only a single coil electrode. In various other embodiments, the lead 14 includes one or more ring electrodes (not shown) along the lead body 22 in lieu of or in addition to the coil electrodes 44, 45. When present, the ring electrodes operate as relatively low voltage pace/sense electrodes. In short, a wide range of electrode combinations may be incorporated into the lead 14 within the scope of the various embodiments of the present invention.

The connector assembly 40 includes a connector 46 and a terminal pin 48. The connector 46 is configured to be coupled to the lead body 22 and is configured to mechanically and electrically couple the lead 14 to a header on the pulse generator 12 (see FIG. 1). In various embodiments, the terminal pin 48 extends proximally from the connector 46 and in some embodiments is coupled to a conductor member (not visible in this view) that extends longitudinally through the lead body 22 such that rotating the terminal pin 48 (relative to the lead body 22) causes the conductor member to rotate within the lead body 22. In some embodiments, the terminal pin 48 includes an aperture extending therethrough in order to accommodate a guide wire or an insertion stylet. In some embodiments (not illustrated), the lead 14 may have a fixed helix 24 that can be secured into tissue by rotating the lead 14 itself, rather than by rotating any internal structure within the lead 14.

In the illustrated embodiment, the distal assembly 42 includes a housing 50, within which the fixation helix 24 is at least partially disposed. In some embodiments, the housing 50 includes or accommodates a mechanism that enables the fixation helix 24 to move distally and proximally relative to the housing 50. In some embodiments, the housing 50 may accommodate or include structure that limits distal travel of the fixation helix 24 (relative to the housing 50). As noted above, the fixation helix 24 operates as an anchoring means for anchoring the distal region 20 of the lead 14 within the heart 16. In some embodiments, the fixation helix 24 is electrically active, and is also used as a helical pace/sense electrode. In some embodiments, the fixation helix 24 is made of an electrically conductive material such as Elgiloy, MP35N, nickel, tungsten, tantalum, iridium, platinum, titanium, palladium, stainless steel as well as alloys of any of these materials. In some embodiments, the fixation helix 24 is made of a non-electrically conductive material such as PES (polyethersulfone), polyurethane-based thermoplastics, ceramics, polypropylene and PEEK (polyetheretherketone).

In some embodiments, the housing 50 may be made of an electrically conductive material such as Elgiloy, MP35N, nickel, tungsten, tantalum, iridium, platinum, titanium, palladium, stainless steel as well as alloys of any of these materials. In some embodiments, the housing 50 is made of a non-electrically conductive material such as PES, polyurethane-based thermoplastics, ceramics, polypropylene and PEEK.

Figure 3:
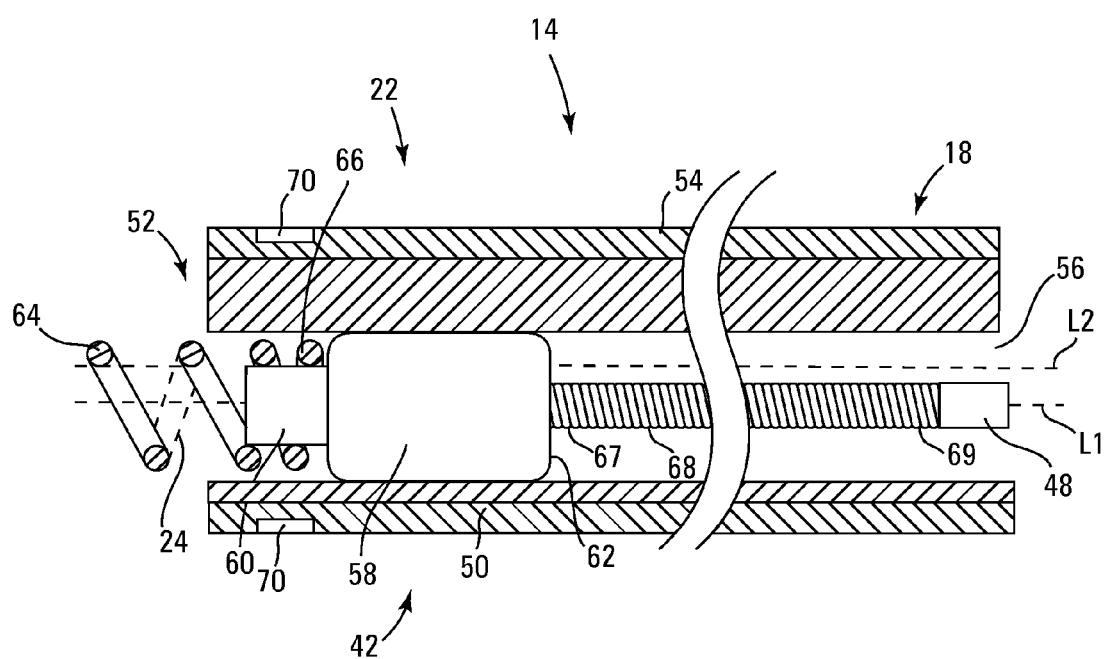
FIG. 3 is a longitudinal cross-sectional view of the lead of FIG. 1.

FIG. 3 is a cross-section of the lead 14. In some embodiments, as illustrated, the lead body 22 includes an inner member 52 and an outer member 54. In some embodiments, the inner member 52 and the outer member 54 may be separately formed and the inner member 52 may subsequently be strung through the outer member 54. The inner member 52 may include several lumens that are configured to accommodate conductive members such as conductive cables or conductive coils and may be configured to accommodate compressive forces that may be applied to the lead 14 while manufacturing the lead 14 without excessively impacting the lumens extending through the inner member 52. Illustrative but non-limiting examples of manufacturing steps in which compressive forces may be applied include stringing the inner member 52 through the outer member 54, stringing other components through the inner member 52 and securing electrodes to the outer member 54.

In some embodiments, as illustrated, the inner member 52 includes a pace/sense lumen 56 as well as several cable lumens (not visible in this illustration). In the illustrated embodiment, the pace/sense lumen 56 has a longitudinal axis $L_1$ that is radially offset from a longitudinal axis $L_2$ of the lead 14. In some embodiments, the cable lumens may extend longitudinally through the inner member 52 within a relatively thicker upper (in the illustrated orientation) portion of the inner member 52.

In the illustrated embodiment, the pace/sense lumen 56 may be configured to accommodate the structure that permits the lead 14 to be actively fixated. In some embodiments, the distal assembly 42 includes a coupler 58 that has a distal portion 60 and a proximal portion 62. In some embodiments, the coupler 58 is formed of a metallic material and is configured to move longitudinally and/or rotationally with respect to the housing 50. In some embodiments, as illustrated, the distal portion 60 may have a relatively smaller diameter (relative to the proximal portion 62) in order to accommodate the fixation helix 24. While not illustrated, in some embodiments the proximal portion 62 is configured to accommodate a seal that provides a seal between the coupler 58 and the housing 50.

A conductor member 68 has a distal region 67 and a proximal region 69. The distal region 67 of the conductor member 68 is secured to the proximal portion 62 of the coupler 58, and extends proximally through the lead body 22 to the connector assembly 40. The proximal region 69 of the conductor member 68 is coupled to the terminal pin 48 such that rotation of the terminal pin 48 causes the conductor member 68 to rotate.

In some embodiments, the conductor member 68 includes or is otherwise formed from a metallic coil. The coupler 58 provides an electrical connection between the conductor member 68 and the fixation helix 24. In some embodiments, the distal region 67 of the conductor member 68 is welded to the proximal portion 62 of the coupler 58. In some embodiments, the proximal region 69 of the conductor member 68 is welded to the terminal pin 48.

The fixation helix 24 has a distal region 64 and a proximal region 66. The proximal region 66 of the fixation helix 24 is secured to the distal portion 60 of the coupler 58. One or more attachment methods are used to secure the fixation helix 24 to the coupler 58. In some embodiments, the proximal region 66 of the fixation helix 24 is welded or soldered onto the distal portion 60 of the coupler 58. In some embodiments, the proximal region 66 of the fixation helix 24 has an inner diameter that is less than an outer diameter of the distal portion 60 of the coupler 58, and thus is held in place via compressive forces. In some embodiments the fixation helix 24 is adhesively secured to the distal portion 60 of the coupler 58. In some embodiments, multiple attachment methods are used.

In some embodiments, the inner member 52 may be made of silicone. The outer member 54 may be formed from a single layer or multiple layer tubular sheath. The outer member 54 may include or otherwise be formed of any suitable material such as polyurethane or silicone. In some embodiments, the outer member 54 may be formed of silicone having a durometer value of 50 or 70.

In the illustrated embodiment, a drug eluting collar 70 is disposed about an exterior of the outer member 54. In various embodiments, the drug eluting collar 56 is configured to provide a time-released dosage of a steroid or other anti-inflammatory agent to the tissue to be stimulated, e.g., the heart tissue in which the electrically active fixation helix 24 is implanted. While not illustrated, in some embodiments the distal assembly 42 may include a radiopaque element disposed under the drug eluting collar 70.

FIG. 4 is a schematic isometric illustration of the inner member 52. The inner member 52 has a distal end 72 and a proximal end 74. In some embodiments, depending on the desired function of the lead 14, the inner member 52 may have a different configuration than that illustrated. For example, the inner member 52 may have a different number or orientation of lumens extending through the inner member 52.

In some embodiments, the inner member 52 extends longitudinally through the lead 14, extending from the housing 50 to the connector assembly 40. In some embodiments, the inner member 52 may only extend partially through the lead 14. In viewing the distal end 72, it can be seen that the inner member 52 includes, in this embodiment, a first cable lumen 76 and a second cable lumen 78. In some embodiments, the first cable lumen 76 and the second cable lumen 78 may have about the same diameter and may, as illustrated, be smaller in diameter than the pace/sense lumen 56. The first cable lumen 76 and the second cable lumen 78 may be configured to accommodate cable conductors that provide shocking current to shocking coils that may be disposed about an exterior of the lead body 22.

In some embodiments, the lumens extending through the inner member 52 may be considered as rendering the inner member 52 symmetrical about a line of symmetry 80 that (in the illustrated orientation) runs vertically across the distal end 72 but not symmetrical about a perpendicular line of symmetry 82 that runs horizontally (in the illustrated orientation) across the distal end 72.

The inner member 52 includes a longitudinally extending crumple zone 84 that is schematically illustrated in this Figure. In some embodiments, the inner member 52 may include a pair of longitudinally extending crumple zones 84, with one arranged on either side of the inner member 52. In some embodiments, the crumple zones 84 are configured to alleviate stress within the inner member 52 that may otherwise be caused during assembly of the lead 14, such as when the inner member 52 is strung within the outer member 54, or the conductor member 68 is strung through the pace/sense lumen 56.

In some embodiments, eliminating or reducing stress within the inner member 52 that may otherwise be caused during assembly of the lead 14 reduces constriction and/or distortion of the lumens. As a result, in some embodiments, the lumens may be made closer in size to the conductive cables or coil conductors that will be strung through the lumens, thereby providing a relatively smaller outside diameter for the lead 14.

Figure 5B:
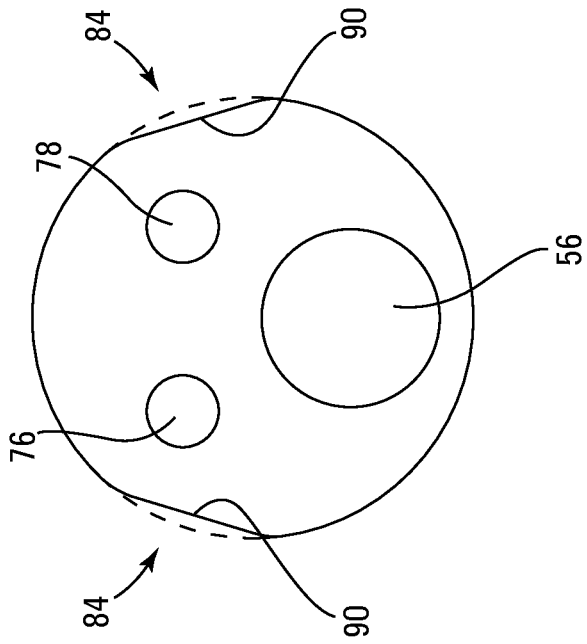
FIGS. 5A and 5B are schematic cross-sectional views of FIG. 4.
Figure 5A:
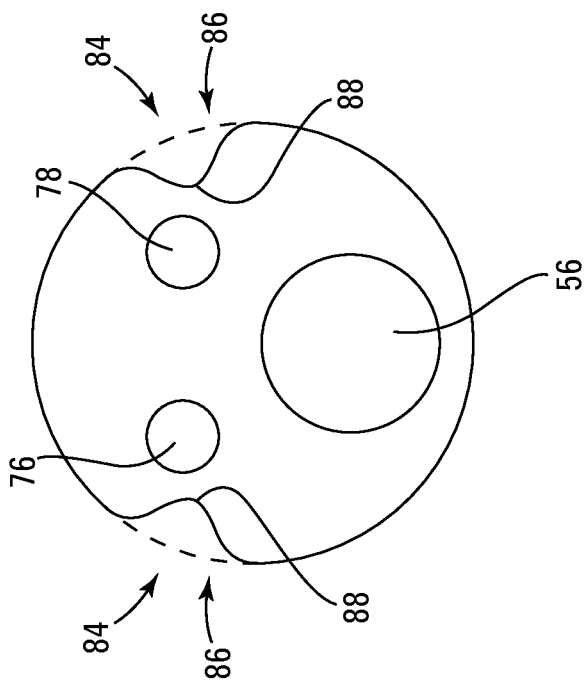

FIGS. 5A and 5B provide illustrative but non-limiting examples of longitudinally extending crumple zones 84. FIG. 5A is a schematic cross-section taken along line 5-5 of FIG. 4. In FIG. 5A, the longitudinally extending crumple zones 84 include or are formed as an elongate groove 86 having an apex 88. A dashed line is shown to illustrate how the crumple zones 84 deviate from an otherwise circular or at least substantially circular cross-sectional profile of an outer surface of the inner member 52. In some embodiments, the elongate groove 86 may have an overall width, measured at an outer surface of the inner member 52, of about 0.008 to about 0.012 inches and a depth, measured perpendicularly to the width, of about 0.010 to about 0.015 inches. In some embodiments, the elongate groove 86 may have an overall width of about 0.0105 inches and a depth of about 0.0145 inches.

In some embodiments, the apex 88 of each elongate groove 86 functions as a hinge point, thereby providing a predetermined stress location away from any of the lumens. As a result, the crumple zones 84 lessen stresses on the inner member 52 adjacent to and/or near or within the lumens and thereby reduce or eliminate distortion of the lumens that may otherwise be caused by compressive forces applied to the lead 14. In some embodiments, the crumple zones 84 may provide void spaces within an interior of the lead 14. In some embodiments, the void spaces may permit the lumens to be made closer in size to the diameters of the coil or cable conductors that will be strung through the lumens as the lumens may undergo less deformation under compressive forces applied to the lead 14.

FIG. 5B is a schematic cross-section taken along line 5-5 of FIG. 4. In FIG. 5B, the longitudinally extending crumple zones 84 are formed as flattened or semi-flattened sides 90 of the inner member 52. A dashed line is shown to illustrate how the crumple zones 84 deviate from an otherwise circular or at least substantially circular cross-sectional profile of an outer surface of the inner member 52. In some embodiments, the inner member 52 may have a diameter measured across the flattened sides 90 that is about 30 percent less than a diameter measured outside of the flattened sides. In an embodiment, the inner member 52 may have an outer diameter of about 0.081 inches measured outside the flattened sides and an outer diameter of about 0.069 inches measured across the flattened sides 90.

In some embodiments, the flattened sides 90 provide void spaces within the lead 14. In some embodiments, the flattened sides 90 reduce stress within or near the lumens, thereby reducing or eliminating distortion within the lumens that may otherwise be caused by compressive forces applied to the lead 14. In some embodiments, the void spaces may permit the lumens to be made closer in size to the coil or cable conductors that will be strung through the lumens as the lumens may undergo less deformation under compressive forces applied to the lead 14.

Figure 6:
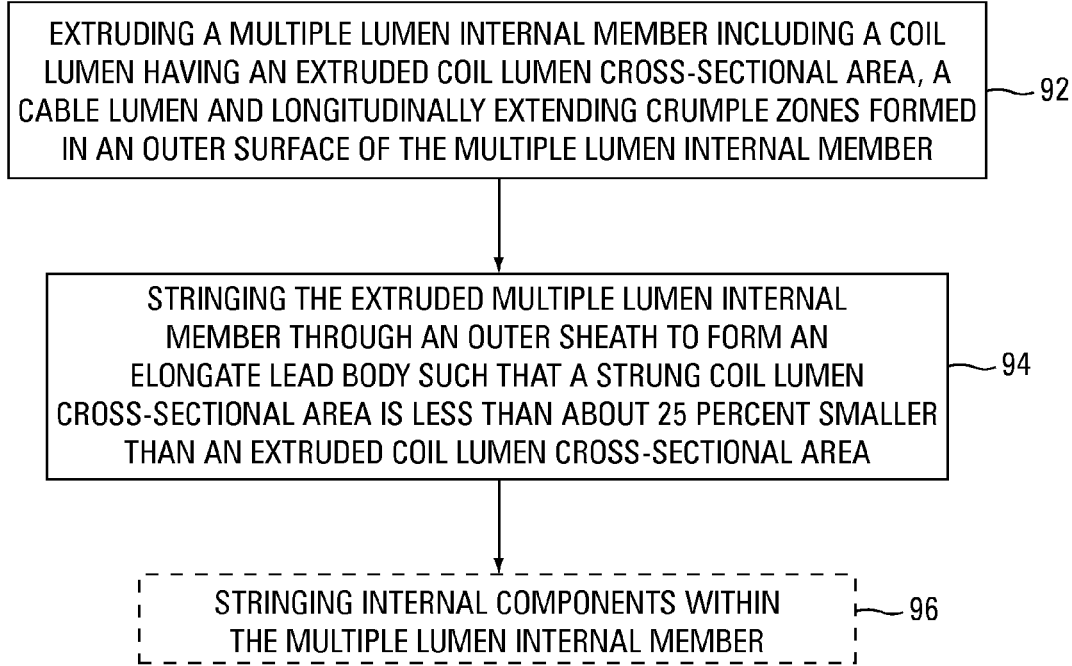
FIG. 6 is a flow diagram illustrating a process for manufacturing the lead of FIG. 1.

FIG. 6 is a flow diagram showing an illustrative method for manufacturing the lead 14. A multiple lumen inner member that includes a coil lumen, a cable lumen and a longitudinally extending crumple zone may be extruded, as generally shown at block 92. The multiple lumen inner member may then be strung through an outer sheath to form an elongate lead body as seen at block 94. In some cases, the coil lumen may be considered as having an extruded cross-sectional area prior to stringing and a strung cross-sectional area after stringing. In some embodiments, the strung cross-sectional area of the coil lumen is less than about 25 percent smaller than the extruded cross-sectional area. In some embodiments, the coil lumen has an at least substantially circular cross-sectional profile both before and after stringing. In some embodiments, the cable lumen has an at least substantially circular cross-sectional profile both before and after stringing.

In some embodiments, as optionally shown at block 96, internal components may also be strung through the multiple lumen inner member. These components may be strung before or after the inner member has been strung through the outer sheath. Examples of internal components include but are not limited to coil conductors, cable conductors, and polymeric liners.

Figure 7:
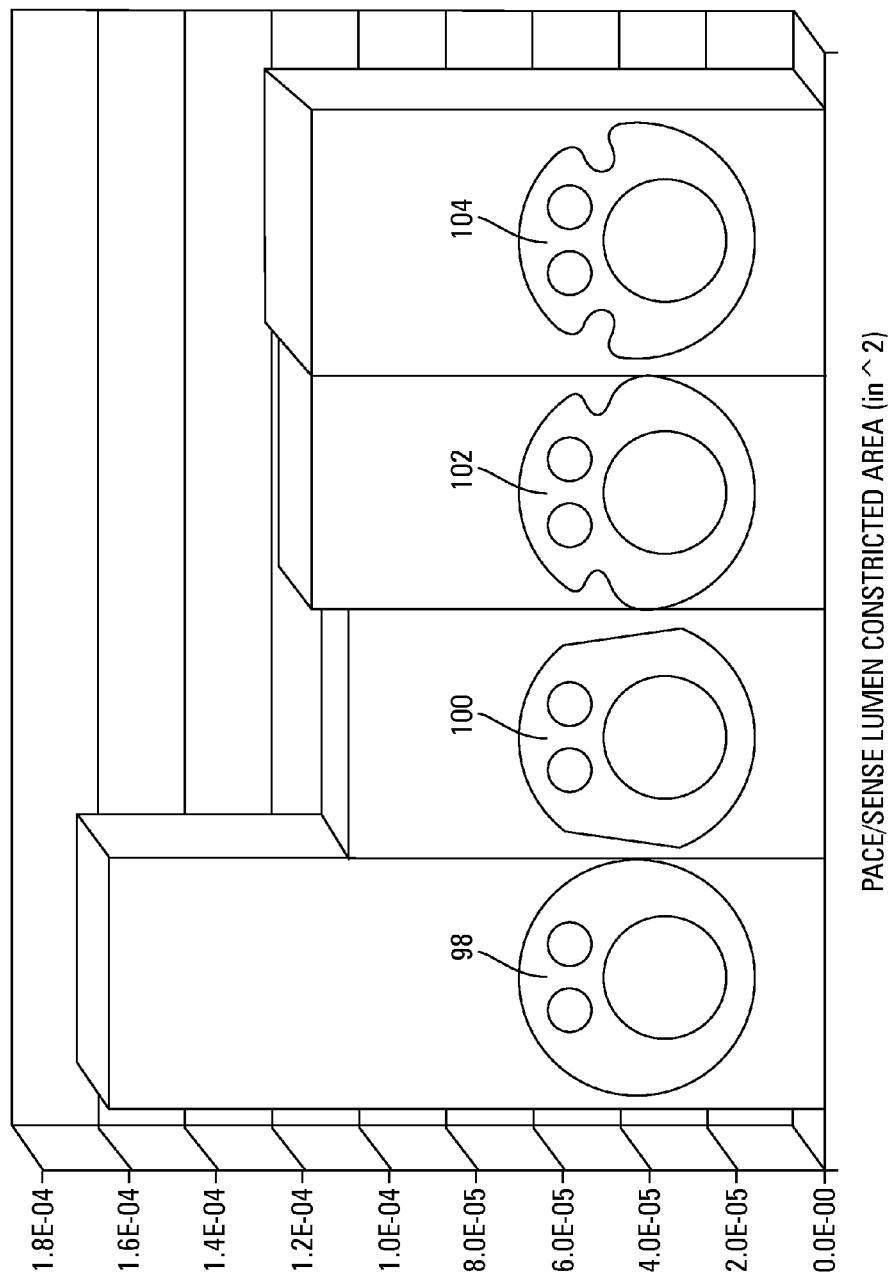
FIG. 7 illustrates improvements in constriction reduction of the pace/sense lumen of the lead of FIG. 1.

FIG. 7 is a schematic illustration of several different configurations for the longitudinally extending crumple zones 84. In this Figure, relative amounts of distortion within the pace/sense lumen 56 are represented as a change in cross-sectional area of the pace/sense lumen 56 as determined using finite element analysis. This information is summarized in the table below.

| Profile Number | Description | Lumen Constriction (square inches) |
| --- | --- | --- |
| 98 | control | 0.000165 |
| 100 | flattened sides | 0.000109 |
| 102 | elongate grooves | 0.000118 |
| 104 | elongate grooves | 0.000122 |

Profile 98 lacks crumple zones and thus serves as a control. In comparison, the profiles including elongate grooves provide a reduction in lumen constriction of about 25 percent. The profile including flattened sides provides a reduction in constriction of about 33 percent. These results can be correlated with FIG. 8, which graphically represents the finite element analysis that was conducted to determine relative stress in and near the pace/sense lumen 56.

Figure 8:
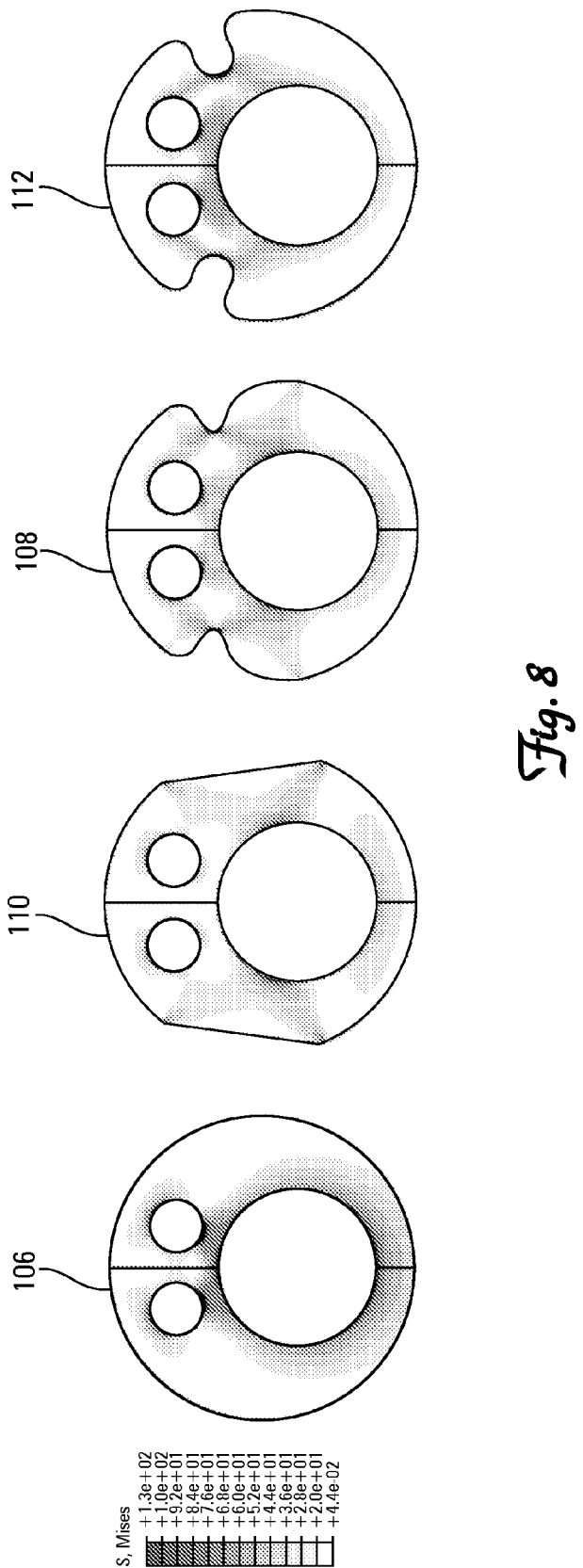
FIG. 8 illustrates reductions in stress around the pace/sense lumen of the lead of FIG. 1.

In the profiles shown in FIG. 8, light or white represents low stress while progressively darker gray area represents increasingly higher levels of stress. In comparing profile 106 (no crumple zones) to either of profile 108 (elongate grooves) or profile 110 (flattened sides), it can be seen that inclusion of the longitudinally extending crumple zones reduces stress in and near the pace/sense lumen. In some embodiments, and with reference to profile 108, it can be seen that there are pinpoint regions with higher stress corresponding to the hinge points previously discussed.

Correlations can be drawn between the lumen constriction results shown in FIG. 7 and the stress analysis shown in FIG. 8. By comparing profile 98 in FIG. 7 with profile 106 in FIG. 8, it can be seen that the control profile has higher regions of stress all around the pace/sense lumen 56 and correspondingly has the highest level of lumen constriction. The other profiles in FIG. 8, showing lower levels of stress around the pace/sense lumen 56, undergo relatively less lumen constriction.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable lead body having a proximal end and a distal end, the implantable lead body comprising:
   an outer sheath extending from the proximal end to the distal end; and
   an asymmetric multiple lumen inner member disposed within the outer sheath, the asymmetric multiple lumen inner member having a longitudinal axis, the asymmetric multiple lumen inner member including:
   a first lumen extending through the asymmetric multiple lumen inner member, the first lumen having a first diameter;
   a second lumen extending through the asymmetric multiple lumen inner member, the second lumen having a second diameter that is less than the first diameter;
   a third lumen extending through the asymmetric multiple lumen inner member, the third lumen having a third diameter that is less than the first diameter; and
   a pair of longitudinally extending crumple zones arranged in an outer surface of the asymmetric multiple lumen inner member.

2. The elongate lead body of claim 1, wherein the first lumen has a longitudinal axis that is offset from the longitudinal axis of the asymmetric multiple lumen inner member.

3. The elongate lead body of claim 1, wherein the asymmetric multiple lumen inner member is symmetric about a first axis extending radially through the first lumen and between the second lumen and the third lumen, and is asymmetric about a second axis extending radially through the first lumen perpendicular to the first axis.

4. The elongate lead body of claim 1, wherein the second diameter is equal to the third diameter.

5. The elongate lead body of claim 1, wherein the pair of longitudinally extending crumple zones are configured to act as hinge points.

6. The elongate lead body of claim 1, wherein the pair of longitudinally extending crumple zones define void spaces between the outer sheath and the inner member.

7. The elongate lead body of claim 1, wherein an outer surface of the inner member has an at least substantially circular cross-sectional profile outside of the pair of longitudinally extending crumple zones.

8. The elongate lead body of claim 1, wherein each of the pair of longitudinally extending crumple zones are arranged on an opposing side of the inner member.

9. The elongate lead body of claim 1, wherein each of the pair of longitudinally extending crumple zones comprise an elongate groove including an apex thereof.

10. The elongate lead body of claim 1, wherein each of the pair of longitudinally extending crumple zones comprise a flattened side of the inner member.

11. The elongate lead body of claim 10, wherein the inner member has a diameter measured across the flattened sides that is about 30 percent less than a diameter measured outside of the flattened sides.

* * * * *